(12) United States Patent
Schomburg

(10) Patent No.: US 6,577,892 B2
(45) Date of Patent: Jun. 10, 2003

(54) APPARATUS FOR PROCESSING BODY SIGNALS

(75) Inventor: Richard A. Schomburg, Hillsboro, OR (US)

(73) Assignee: Biotonik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 325 days.

(21) Appl. No.: 09/788,756

(22) Filed: Feb. 19, 2001

(65) Prior Publication Data

US 2001/0021814 A1 Sep. 13, 2001

(30) Foreign Application Priority Data

Feb. 18, 2000 (DE) .......................... 100 08 792

(51) Int. Cl.[7] .................................. A61B 5/04
(52) U.S. Cl. .................... 600/509; 600/300; 600/523
(58) Field of Search ........................ 600/300, 301, 600/309, 310, 322, 323, 324, 336, 341, 473, 476, 508, 509, 515, 516, 517, 518, 523; 128/923; 702/71, 72, 75, 76; 708/3, 306, 308, 422, 423

(56) References Cited

U.S. PATENT DOCUMENTS

| | | | |
|---|---|---|---|
| 4,776,339 A | * | 10/1988 | Schreiber .................... 600/324 |
| 4,928,692 A | * | 5/1990 | Goodman et al. ........... 600/324 |
| 5,014,701 A | | 5/1991 | Pless et al. |
| 5,306,293 A | | 4/1994 | Zacouto |
| 5,439,483 A | | 8/1995 | Duong-Van |
| 5,494,032 A | * | 2/1996 | Robinson et al. ........... 600/323 |
| 5,778,881 A | | 7/1998 | Sun et al. |
| 5,857,462 A | * | 1/1999 | Thomas et al. ............. 600/310 |
| 5,924,979 A | * | 7/1999 | Swedlow et al. ........... 600/300 |
| 5,960,373 A | * | 9/1999 | Fukuda et al. .................. 702/76 |
| 6,083,172 A | * | 7/2000 | Baker, Jr. et al. ........... 600/300 |
| 6,094,592 A | * | 7/2000 | Yorkey et al. .............. 600/310 |
| 6,339,715 B1 | * | 1/2002 | Bahr et al. ................... 600/323 |
| 6,520,920 B2 | * | 2/2003 | Nissila et al. ................ 600/300 |

FOREIGN PATENT DOCUMENTS

| | | |
|---|---|---|
| DE | 197 52 094 C1 | 7/1999 |
| DE | 199 38 376 A1 | 2/2001 |
| DE | 199 63 246 A1 | 6/2001 |
| EP | 0 487 429 A1 | 5/1992 |
| JP | 3-15439 A * | 1/1991 |

* cited by examiner

Primary Examiner—Willis R. Wolfe
(74) Attorney, Agent, or Firm—Hahn Loeser + Parks LLP; Stephen L. Grant

(57) ABSTRACT

Apparatus for processing body signals, comprising at least one sensor (10, 12) for picking up in particular electrical signals from a living body, and means (16, 18) for preparing picked-up signals for further processing, and at least one first memory (22) for a picked-up measurement signal or signal portions, comprising at least one second memory (26) which contains a predeterminable comparison signal which is finite in respect of time, and signal comparison means (24) which are connected to the second memory (26) and the first memory (22) and which are adapted for sliding comparison of signal portions, which overlap in respect of time, of the measurement signal in the first memory (22) to the comparison signal stored in the second memory (26) and for output of a correlation coefficient representing the similarity of each compared signal portion of the measurement signal to the comparison signal.

15 Claims, 6 Drawing Sheets

$$g(z) := -\left(z \exp\left(\frac{-z^2}{2}\right)\right)$$

$$g(z) := -\left[(z^2 - 1) \cdot \exp\left(\frac{-z^2}{2}\right)\right]$$

$$g(z) := \text{if}\left(.75 \leq |z| \leq 1.25, \frac{1 + \cos(4 \cdot \pi \cdot z)}{2}, 0\right) - \text{if}\left[-5 \leq z \leq 5, \left(\frac{1 + \cos\left(\frac{\pi \cdot z}{5}\right)}{20}\right), 0\right]$$

APPARATUS FOR PROCESSING BODY SIGNALS

The invention concerns an apparatus for processing body signals, which includes a sensor for picking up in particular electrical signals from a living body, and means for preparing picked-up signals for further processing, and at least one first memory for a picked-up measurement signal or signal portions.

BACKGROUND OF THE ART

It is frequently a matter of concern to identify given features in for example electrically recorded signals. For example, it may be a matter of interest to identify T-waves or QRS-complexes in an electrocardiogram and to determine as accurately as possible the time at which they occur. To analyse such signals, it is desirable to locate certain events or signal features, from the point of view of time.

With that background in mind, the present invention is concerned in particular with picking up intracardially recorded signals, in particular in an implanted device. For reasons relating to power requirement and the limited amount of space involved, only restricted resources for signal processing and analysis are available in an implanted device.

Various apparatuses and methods of feature identification of heart signals and for signal analysis are already known. European patent No 0 487 429 for example discloses an apparatus in which is stored a sequence of values of such parameters which correspond to an active cardiac cycle. The apparatus includes comparison devices to compare the stored parameter values of the active cardiac cycle to previously stored items of information about those values and, in the event of a positive comparison result, to trigger a signal. German patent applications Nos 199 38 376 and 199 63 246 which are not prior publications also concern apparatuses in which a measured cardiac signal is compared to previously formed and stored comparison signals in order in the case of DE 199 38 376 to identify fusion events in the electrostimulation of the heart and in the case of DE 199 63 246 to detect the circulatory effect of extrasystoles.

U.S. Pat. No. 5,439,483 also discloses the use of a wavelet transform for the classification of tachycardias. In U.S. Pat. No. 5,778,881 a wavelet transform is additionally combined with a hidden Markov modelling in order to be able to detect P-R-waves in each case as Markov states with a reduced number of wavelet coefficients. It is further proposed therein that a set of wavelet coefficients, which is typical for the respective result, can be automatically updated in the event of rapid changes in the signal morphology, in order to make the analysis independent of short-term fluctuations in the physiological signals for example due to physical stress.

The aim of the present invention, in physiological signals such as intracardial electrocardiograms (ECG) and intracardial dynamic impedance patterns (IDZ), is to determine the occurrence of certain features and the moments in time thereof, hereinafter also referred to as time location, in an efficient manner. That should be effected as reliably as possible even in the presence of noise and interference signals. The degree of accuracy of time location of a feature is to correspond to the sampling rate, that is to say the time raster with which the physiological signals are recorded. Feature recognition is also to function in the event of a variation in signal morphology.

Further aims of the invention concern improved feature analysis functions.

Therefore the object of the present invention is to permit better or more efficient signal analysis in comparison with the state of the art at least in individual areas and thus very substantially to attain the above-indicated aims.

SUMMARY OF THE INVENTION

In accordance with the invention, that object is attained by an apparatus of the kind set forth in the opening part of this specification, which includes at least one second memory which contains a predeterminable comparison signal which is finite in respect of time, and signal comparison means which are connected to the second and the first memories and which are adapted for sliding or continuous comparison of signal portions, which overlap in respect of time, of the measurement signal in the first memory to the comparison signal stored in the second memory and for output of a correlation coefficient representing the similarity of each compared signal portion of the measurement signal to the comparison signal.

The integral of the comparison signal in relation to time or its sum of time-discrete signal values is preferably zero. In that way, the correlation signal formed by the correlation coefficients is a signal which is of a mean value of about zero. That greatly simplifies subsequent signal analysis.

In this case, the measurement signal is preferably an intracardial electrogram (ECG) or an intracardially recorded dynamic impedance pattern (IDZ). If those signals are not recorded continuously but in time-discrete manner with a sampling rate, the first memory has a sequence of time-discrete measurement values representing the measurement signal. The comparison signal is also stored in the second memory as a finite sequence of time-discrete values. In that case, instead of the integral of the comparison signal in respect of time preferably its sum of all discrete signal values is zero. That complies with the requirements made in relation to wavelets. Therefore the comparison signal can also be referred to as a comparison wavelet.

A crucial difference in relation to the wavelet transform is that the apparatus does not provide a two-dimensional result, like the wavelet transform, as the comparison pattern is not subjected to time scaling for the investigation of each measurement signal portion over a given frequency range. That decisively reduces the computing power required.

The level of resolution in respect of time of the measurement signal in the first memory is preferably the same as that of the comparison signal in the second memory. Each measurement signal portion to be compared to the comparison signal then corresponds to the comparison signal, in respect of the time duration and the number of discrete measurement values. The correlation coefficients formed by the comparison of the signals also form a sequence of time-discrete values which respectively represent the similarity of precisely one signal portion in the first memory to the comparison signal. The corresponding signal portions of the measurement signal in the first memory preferably overlap in that case in such a way that they are displaced relative to each other only by a discrete time step corresponding to the time resolution of the measurement signal. Due to this sliding comparison, the procedure produces a time-discrete correlation signal which is formed by the correlation coefficients which occur in succession in respect of time, as the result of comparison of the signals. The level of time resolution of the correlation signal is then the same as that of the measurement signal and the comparison signal. The correlation signal however can also be formed with a lower level of time resolution if the comparison operation is implemented only for each second, third or n-th time step. The measurement signal portions which are used for comparison with the comparison signal are then displaced relative to each other from one comparison operation to another comparison operation in each case by two, three or n time steps. In a practical context however it will frequently be advantageous to record the measurement and the comparison signals with a correspondingly lower sampling rate which defines the time raster, if the lower level of time resolution of the signal still permits secure feature identification and reliable signal comparison.

An essential feature of the apparatus is the second memory which contains the comparison signal which can be predetermined in accordance with the respective signal feature to be detected and in particular is variable for adaptation to a varying signal morphology by the apparatus itself.

A preferred apparatus is one in which the signal comparison means are connected to a logarithm storage means or memory which contains tables of logarithms for values of the measurement and the comparison signals, in which respect the signal comparison means are adapted to form the correlation coefficients in such a way that they effect multiplication of a value of the comparison signal from the second memory by the corresponding value of the first measurement signal from the first memory, in such a way that firstly the logarithms of the values themselves to be multiplied or the values which are respectively closest thereto are read out of the logarithm memory and then the two logarithms are added.

A procedure of that kind which is known per se, by the use of logarithm tables or slide rules for the multiplication of two values can be effected in an efficient, memory-saving fashion.

A preferred apparatus further has detection means which are connected to the signal comparison means and which are adapted to detect maximum values and/or zero-passages of a signal formed by the correlation coefficients.

Preferably, the apparatus also has threshold value comparison means which are connected to the signal comparison means and a threshold value memory containing a threshold value and which are adapted to output an identification signal as soon as the correlation coefficient outputted by the signal comparison means exceeds the threshold value. In that case, the apparatus is preferably of such a configuration that the threshold value comparison means are so designed that they output an identification signal when a correlation coefficient for a first signal portion from the first memory exceeds the threshold value and for a second signal portion which is recorded in terms of time after the first signal portion reaches the value zero or is below that value. In addition, there are preferably provided locating means which are connected to the threshold value comparison means and the detection means and are so designed that they associate a location signal with that measurement signal portion in the first memory, for which the signal formed by the correlation coefficient is at a maximum within that section of the signal formed by the correlation coefficient, in respect of which the threshold value comparison means output an identification signal.

As each correlation coefficient of the sequence of correlation coefficients is associated precisely with a signal portion of the measurement signal stored in the first memory, it is possible, by determining the corresponding maxima of the sequence of correlation coefficients, to determine precisely the time location, that is to say the location of a feature in the signal being investigated and thus the time at which a feature occurs.

The apparatus further preferably has threshold value-forming means which are connected to the threshold value memory and the locating means and which are so designed that they form a new threshold value after the occurrence of a location signal in such a way that the correlation coefficient associated with the location signal is involved in a weighted condition in the formation of the new threshold value. That permits continuous adaptation of the threshold value to the actual configuration of the measurement signal and to changes in the morphology thereof.

Also preferred is an apparatus which has comparison signal-forming means for forming a new comparison signal, which are connected to the second memory and which are so designed that a measured signal portion corresponding to a signal feature to be detected is transformed to the comparison signal in such a way that its integral in relation to time or the sum of the time-discrete signal values is zero, and the comparison signal formed in that way is transferred into the second memory. The comparison signal-forming means thus permit automatic formation of a suitable comparison signal.

A preferred apparatus is also one which includes comparison signal-adaptation means for adaptation of the comparison signal, which are connected to the first memory, the second memory and the locating means and which are so designed that they form a new adapted comparison signal when the locating means output a location signal, wherein the adapted comparison signal is formed using that measurement signal portion from the first memory with which the location signal is associated. That permits continuous adaptation of the comparison signal to the actual morphology of the measurement signal, with the consequence that characteristics of the measurement signal are reflected in the comparison signal so that the comparison signal can also be analysed, instead of the measurement signal, for analysis of the measurement signal. Furthermore, that adaptation of the comparison signal permits secure, reliable and time-accurate feature detection.

In this respect the apparatus is preferably distinguished by comparison signal-adaptation means which are so designed that the comparison signal which is valid prior to the adaptation operation, for formation of the comparison signal which is valid after the adaptation operation, is involved, multiplied with a weighting factor of 1-$\alpha$, in the comparison signal which is to be freshly formed, while that signal portion in the first memory, with which the location signal for triggering adaptation of the comparison signal is associated, is involved with a weighting factor of $\alpha$ in the comparison signal which is valid after the adaptation operation. In that respect, $\alpha$ is a value of between 0 and 1. The new comparison signal then corresponds to the sum of the two weighted signals which are involved in the formation of the new comparison signal.

The comparison signal-forming means and/or the comparison signal-adaptation means are preferably also so designed that the comparison signal which is formed or adapted is standardised in such a way that the amplitude thereof corresponds to the maximum amplitude of the measurement signal. That avoids unwanted effects as a consequence of signal multiplication in the formation of the correlation coefficients, which would cause square distortion of the scale for the threshold value.

Preferably the apparatus has a database which contains a plurality of comparison signals and which is connected to the second memory in such a way that comparison signals can be transferred from the database into the second memory and vice-versa. In that way, the apparatus can operate with various comparison signals for the detection of various signal features.

In addition, the apparatus preferably has analysis means which are designed to analyse the characterising properties of the preferably adapted comparison signal. Analysis means of that kind permit analysis of the measurement signal indirectly by evaluation of the comparison signal which is adapted to the measurement signal.

In a preferred variant the apparatus includes means for recording two cardiac signals of which one is associated with the left ventricle or atrium and the other is associated with the right ventricle or atrium, and means connected to said recording means for forming a bimodal signal from the two cardiac signals, in such a way that the bimodal signal contains a feature of the first signal prior to its conduction into the respective other ventricle or atrium and the corresponding feature after its conduction, so that the feature is contained in the bimodal signal at a spacing in respect of time corresponding to the conduction time, on the one hand in its form prior to conduction and on the other hand in its form after conduction. In addition the second memory of that apparatus contains a bimodal comparison signal which can be adapted to the bimodal signal so that, after adaptation of the bimodal comparison signal to the bimodal signal, the conduction time can be determined by analysis of the comparison signal. In the context of the described apparatus, that permits highly accurate determination of the conduction time between two heart chambers.

BRIEF DESCRIPTION OF THE DRAWINGS

The invention will now be described in greater detail by means of an embodiment with reference to the drawings in which.

DETAILED DESCRIPTION OF THE INVENTION

Figure 1:
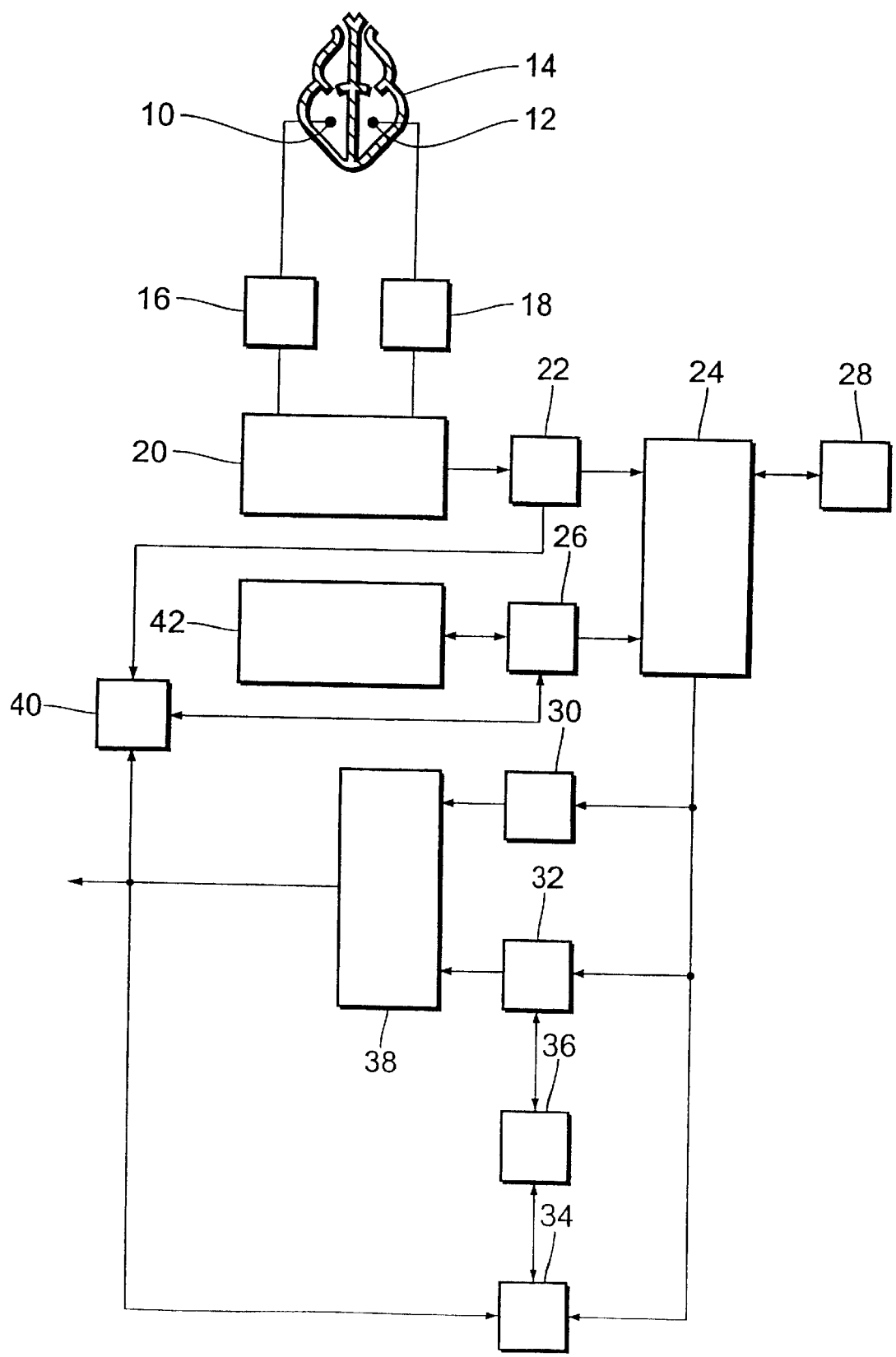
FIG. 1 shows a block circuit diagram of an apparatus according to the invention.

The block circuit diagram shown in FIG. 1 illustrates two signal pick-ups 10 and 12 which are each placed in the left and right ventricles respectively of a heart 14. A respective measurement amplifier 16 and 18 is connected to each of the signal pick-ups 10 and 12. By way of the amplifiers 16 and 18, the signal which is recorded by the measurement value pick-ups 10 and 12 passes into a measurement signal preparation unit 20 which is connected to a first memory 22 for the measurement signal and which writes thereinto selectively a time-discrete sequence of measurement values which represent either the measurement signal from the left or the right ventricle or a bimodal measurement signal which is made up of the two. The first memory 22 is connected to a correlation signal-forming means 24 which in turn is also connected to a second memory 26 for a comparison signal and a logarithm memory 28. The correlation signal-forming means 24 forms a time-discrete correlation signal in a manner described in greater detail hereinafter, and transmits it to a detector 30, an identification unit 32 and a threshold value-forming means 34. The detector 30 is adapted to detect local maxima and the zero-passages of the correlation signal while the identification unit 32 outputs a signal as soon as the correlation signal assumes a greater value than is stored in a threshold value memory 36 connected to the identification unit 32. The threshold value memory 36 is also connected to the threshold value-forming means 34. The threshold value-forming means 34 contains a memory for the previously described weighting factor α.

The detector 30 and the identification unit 32 are each connected on their output side to a location detector 38 which in the manner described hereinbefore outputs a location signal when the correlation signal has a local maximum above the threshold value, followed by a zero-passage. The location signal is precisely associated with a defined portion of the measurement signal in the first memory 22. The location detector 38 is connected on the output side both to the threshold value-forming means 34 and also to a comparison signal-forming means 40. The comparison signal-forming means 40 includes a memory for the values of the parameters β and γ, described hereinafter, for comparison signal adaptation.

In response to a location signal from the location detector 30, the threshold value-forming means forms in the manner described elsewhere from the value of the correlation signal associated with the location signal and threshold values stored in the threshold value memory 36 a new threshold value and stores it instead of the old one in the threshold value memory 36.

In a similar manner, the location signal from the location detector 38 triggers the formation of a new comparison signal in the comparison signal-forming means 40. The comparison signal-forming means 40 forms the new comparison signal which involves, weighted in each case, the old comparison signal and that measurement signal portion which is associated with the location signal. The old comparison signal is then replaced by the new one in the second memory 26. The second memory 26 is also connected to a database 42 which contains various comparison signals for various features of the measurement signal, which are to be detected.

The described components of the apparatus can be at least in part implemented by software modules and a microprocessor.

The apparatus involves using correlation methods which in part recall applications of the wavelet transform, while however differing therefrom in various important points. That is described in the following paragraphs.

In simple terms, the wavelet transform is a mathematical method which is applied to an input function, for example a voltage signal, which is the function of an independent variable, for example time. For the wavelet transform, use is made of a specific signal which is limited in respect of time, the wavelet, which is a function of the same independent variable as the input function. The wavelet transform produces a two-dimensional result which reflects the frequency response of the input function, plotted in relation to time. That frequency response is described by a procedure whereby a wavelet, in a parameter range of interest, is scaled in relation to the independent variable, therefore for example in respect of time and thus spectrum, and the output wavelet which is scaled in that way is compared to the input function.

The frequency axis of the two-dimensional result of the wavelet transform corresponds in that case to the scaling factor of the wavelet, while the higher frequencies are plotted further away from the origin of a co-ordinate system. Each point of the two-dimensional output function has the value of a correlation coefficient which reflects the correlation of the input signal at the corresponding time with that wavelet which is associated with the corresponding scaling factor. In that way, the wavelet transform affords a two-dimensional output function which reflects the similarity between an input function or an input signal and a respectively variously scaled wavelet, wherein one co-ordinate of the two-dimensional output function is the scaling factor of the wavelet and the other co-ordinate is the independent variable of the input function, for example time.

In the case of continuous input signals or functions, the wavelet transform can be described by the following equation:

$$w(s,\tau) = \int f(t) * \Psi(st+\tau) dt$$

In that function, $\Psi$ is a continuous 'mother wavelet' function which depends on a scaling parameter s and a translation parameter $\tau$. In order to be a wavelet, the function must have a mean value of zero and fall with increasing values of its argument in order to be located in respect of time and frequency. The illustrated integration only has to be implemented over the time domain, for which the coefficients of $\Psi$ are not equal to zero.

For discrete input functions or signals the wavelet transform can be expressed by the following formula:

$$W(s, n\tau) = \sum_k f(\tau(n+k)) * \Psi(k)$$

In that formula n is a numerator for a sampling value, $\tau$ is the sampling interval and k is an index for the sampling value counter of the wavelet $\Psi$ with the scaling factor s.

For a system with discrete input functions, the correlation function between an input signal and a predetermined (comparison signal or also a correlation signal or correlation wavelet), $\Psi$, can be expressed as:

$$C(n\tau) = \sum_k f(\tau(n+k)) * \Psi(k)$$

Therein n is the number of the sampling value, $\tau$ is the sampling interval and k is an index for the sampling value number of the wavelet. By comparison of the last two equations it will be clear that the correlation function can be viewed as a particular case of the wavelet transform for which the scaling factor s is constant.

The apparatus is based on methods which include calculation and interpretation of correlation functions for which one or more comparison signals or correlator wavelets are not constant but are adapted so that they better correspond to features in the signal to be processed. That differs from predetermined temporal or spectral scaling of a predetermined fixed mother wavelet, as is used for the wavelet transform. Within the apparatus set forth herein, adaptation of the comparison signal can concern all aspects of the signal form and proceeds with continuing processing of the measurement signal and the corresponding calculation of the correlation coefficients. Thus the comparison signal in the apparatus essentially only has in common with a wavelet the fact that its integral in respect of time is zero or correspondingly the sum of its discrete time values is zero. If necessary further limitations can be provided in regard to the form of the comparison signal.

The following principles apply in regard to the correlation functions as are used in the apparatus set forth herein:
1. Calculation of the correlation function is implemented in the time domain.
2. The correlation function of an input or measurement signal has the same time scale as the measurement signal.
3. The correlation function has a given value for each discrete value of the measurement signal.
4. The correlation function is based on a comparison signal (correlator wavelet) which is also a function of time.
5. The integral of the comparison signal in relation to time should be zero; in the case of a time-discrete comparison signal the sum of the signal values should be zero.
6. The comparison signal can be derived from a known or expected feature of the measurement signal. In that case, the correlation function will always have maxima where the feature is contained in the signal, including those locations in the measurement signal at which the feature suffers from noise.
7. Each value of the correlation function is equal to the correlation coefficient between the measurement signal at the corresponding time and the comparison signal. In that way the value of the correlation functions shows for each moment in time, how greatly the measurement signal is similar to the comparison signal at that time.

Counterparts of correlation functions in the frequency domain:
1. Each signal processing in the time domain has an equivalent in the frequency domain.
2. The application of the correlation function in the time domain corresponds to band pass filtering. Because the integral of the comparison signal is zero the dc gain of that equivalent filter is zero.
3. The band pass filter which corresponds to the correlation function is a digital FIR-filter (FIR=finite impulse response) in which the number of the coefficients corresponds to the number of the discrete signal values which form the comparison signal.
4. The band pass filter corresponding to the correlation function is, for the number of signal values of the comparison signal, an optimum filter for such features within the measurement signal, which resemble the comparison signal.
5. The band pass filter corresponding to the correlation function is automatically adapted when details of the comparison signal are modified, as in the adaptation to variations of known measured features of the measurement signal.

The measurement signal is at least put into intermediate storage in the first memory 22. In that respect the intermediate memory can be an FIFO-memory and makes it possible for the measured signal to be processed not only in real time but also later. The size of the first memory or intermediate memory 22 depends on the ratio of the sampling rate to the processor speed and is further influenced by the statistical properties of the measurement signal. Typically, the first memory or intermediate memory 22 for an ECG-signal is of such a size that it can receive the measurement values of a signal of approximately one second in length. Management of the first memory 22 is implemented by way of an index indicator as is described in greater detail hereinafter.

A point of particular significance is the choice of the comparison signal iWav which is firstly to be predetermined. Important parameters are in this respect the length of the comparison signal and its shape.

The length of the comparison signal, wLen, directly influences both the greatest width (extension in respect of time) of the features to be detected, and also the required computing capacity. In simulation of an apparatus for processing a measurement signal of a heart chamber at a sampling rate of 250 Hz corresponding to a time raster of 4 ms, a comparison signal length of 16 signal values has been found to be appropriate. From the time point of view, that corresponds to a duration of the comparison signal of 64 ms. If however a single ECG-channel contains signals from two chambers, such as for example from the right and left atrium, additional comparison signals can be required in order to cover the combined signals.

Figure 2:
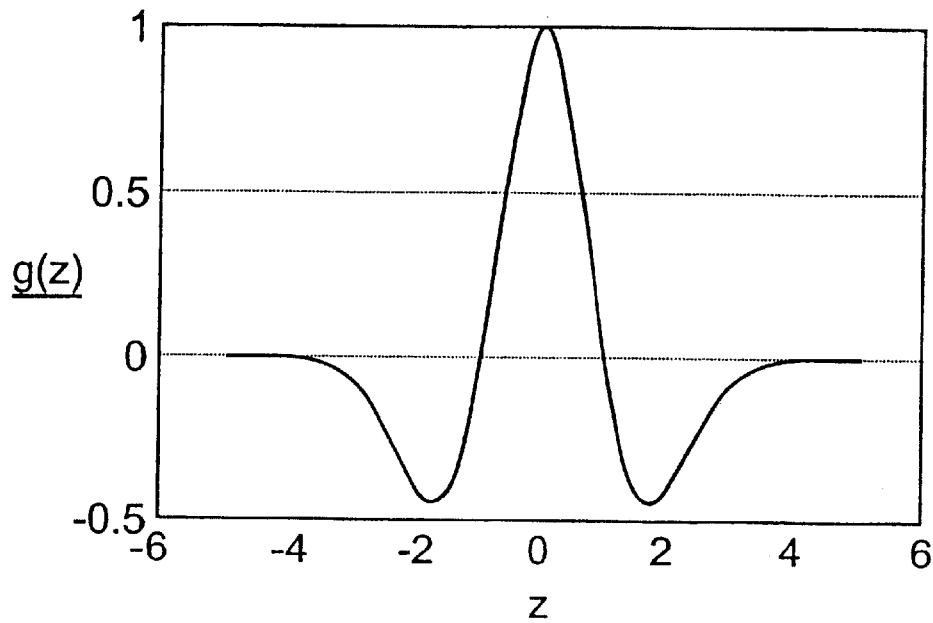
FIG. 2 shows a comparison signal in the form of a wavelet of 'Mexican hat' type.
Figure 3:
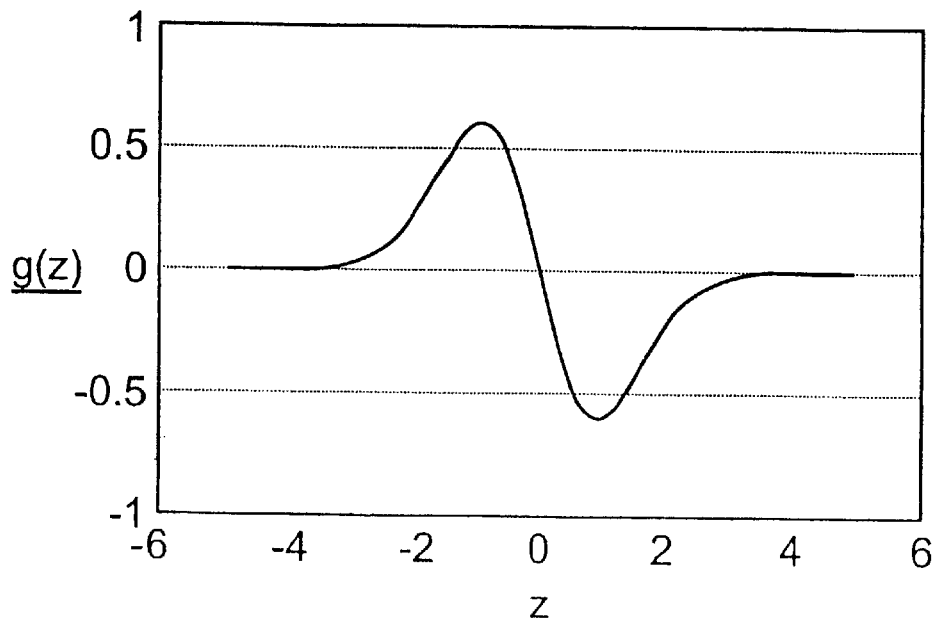
FIG. 3 shows a comparison signal in the form of an asymmetrical wavelet.
Figure 4:
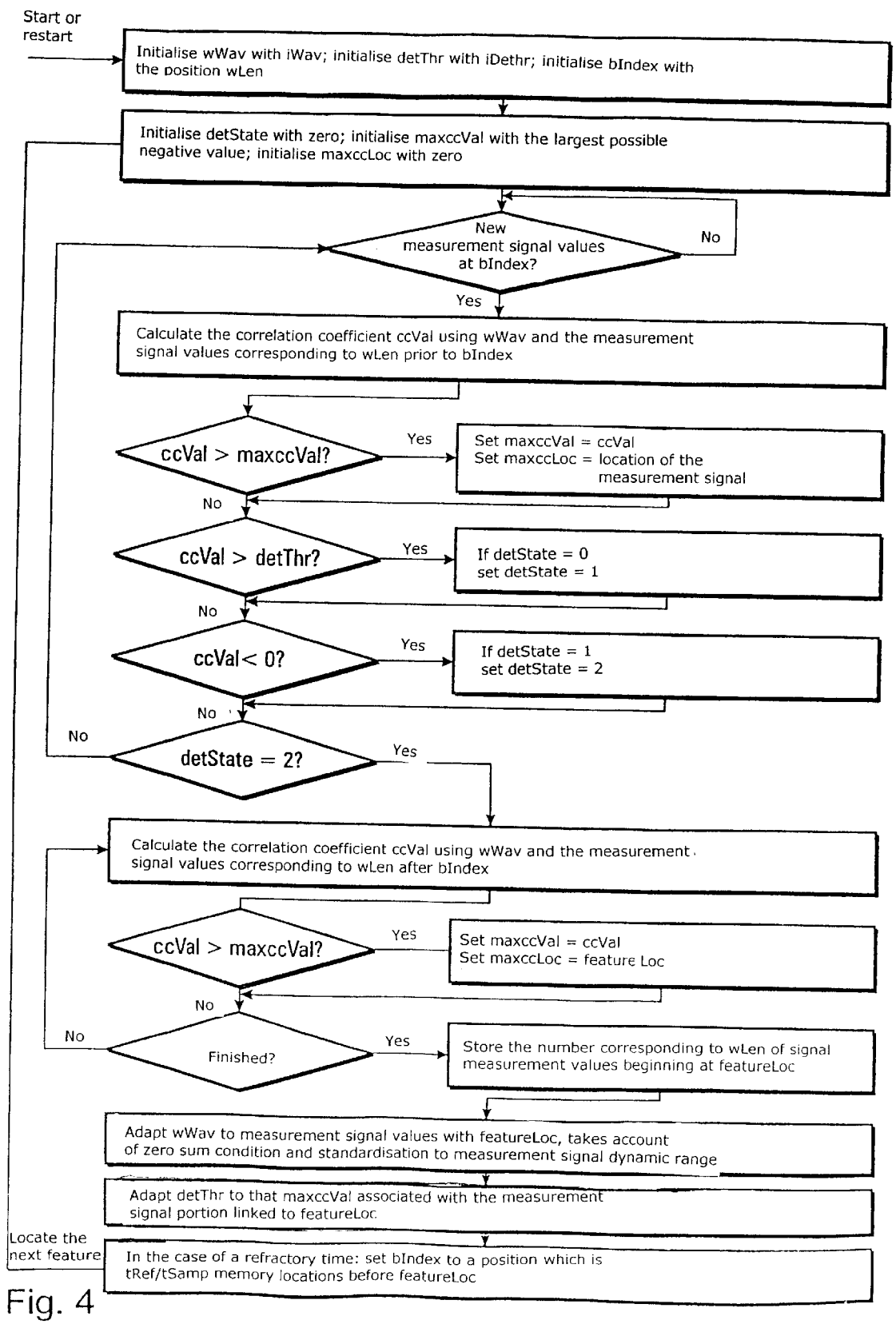
FIG. 4 shows a flow chart of a detection/location algorithm.

An aspect of great significance is also the initially predetermined shape of the comparison signal which is stored in the memory 26. Besides that one comparison signal, it is also possible for further comparison signals to be stored in the database 40. The shape of the at least one comparison signal is established by estimating the signal shape of that signal feature in the measurement signal, which is to be detected as a matter of priority. Alternatively however, the comparison signal may also be of a standard shape, like the wavelets of 'Mexican hat' type or asymmetrical type, as shown in FIG. 2 or FIG. 3.

If such a standard wavelet is used as a comparison signal, its time scaling should approximately correspond to the duration of the expected feature. At any event, the initially selected comparison signal should correspond to the dynamic range of the measurement signal. In addition the sum of the signal values of the comparison signal should be zero.

In the situations of use of the invention which are of interest, the apparatus is used for directly measuring comparable signal features. Such an example is described hereinafter and concerns measurement of the time relationships between two-chamber electrocardiograms. For that purpose, the initial comparison signal iWav can be of a particular shape and calculation of the correlation coefficients can be effected for signals of a plurality of data channels. Operation of the apparatus with an initially set comparison signal will generally occur in the context of clinical use when such an apparatus is implanted. Subsequent treatment procedures are normally effected using an adapted version of the originally set comparison signal which reflects the properties of the existing ECG-signals or IDZ-signals of a patient. Signal processing can however automatically revert to use of the comparison signal as originally set, more specifically in the context of a strategy for the recovery of data in the event of a detection loss, that is to say when no signal features are further detected. That can happen if the morphology of the measurement signal changes greatly within a short time.

A particular property of the apparatus is its capability of adapting the comparison signal to located or detected signal features of the measurement signal.

The degree of adaptation of the comparison signal is controlled by the parameter $\alpha$ which is stored in the apparatus. Suitable values of $\alpha$ have been found to be those of the order of magnitude of $\frac{1}{16}$. That is advantageous for the reason that multiplication by $1-\alpha$ (see below) can be implemented in a simple fashion by bit shift and subtraction in the form of a shift-and-subtract operation.

If adaptation of the comparison signal is required, the comparison signal wWav is replaced by one which is the sum of the comparison signal to be set multiplied by $(1-\alpha)$ and the corresponding signal value of the last-located feature of the measurement signal multiplied by $\alpha$. The adaptation which results therefrom exhibits exponential weighting of preceding features. Adaptation of the comparison signal which is defined in the time domain corresponds in the frequency domain to adaptation of the form of a corresponding band pass filter for optimum extraction of the features of the measurement signal, which are to be detected.

Although adaptation of the comparison signal for each located feature can occur within a cardiac cycle that is generally not required. On the contrary, it is preferred for adaptation to be effected at predetermined moments in time, for the establishment of which the physiological characteristics in respect of time of the features which are of interest, and the parameters to be extracted therefrom, are to be taken into account. Alternatively, adaptation can be triggered in reaction to changes in the magnitude of the local maxima of the correlation function, which occur upon location of a feature to be detected. The possibility of adaptation in each cardiac cycle can however be valuable immediately following implantation of the apparatus and in other situations where rapid adaptation to existing measurement signals of a given patient is wanted, in particular in the case of a detection loss.

The adapted comparison signals must also satisfy the conditions that the sum of the discrete signal values of which the comparison signal is composed is zero. This adaptation operation is effected in a second adaptation step and preferably involves the smaller signal values, whereby the influence on the calculated values of the correlation coefficient is minimised.

Preferably the dynamic band width of the adapted comparison signal wWav is adapted to the maximum amplitude of the measurement signal, as is determined by the measurement channel. In other words, the dynamic range of the comparison signal is standardised to the maximum dynamic range of the measurement signal. That avoids quadratic distortion of a scale for a threshold value for the correlation coefficient which would otherwise be involved with variations in the measurement signal amplitude.

The threshold value for the correlation coefficient which is used for location of signal features to be detected is also preferably adapted to the actual conditions by the apparatus with the passage of time.

Adaptation of the threshold value detThr is determined by a parameter $\beta$ describing the degree of adaptation and by a limit value asymptote $\gamma$. Both $\beta$ and also $\gamma$ should be of values <1 and are stored in a memory of the apparatus. Simulations have shown that usable values for $\beta$ are in the order of magnitude of $\frac{1}{8}$ while usable values for $\gamma$ are of an order of magnitude of $\frac{1}{2}$. In the simulation, those values were found to be usable for the reason that they permitted feature detection even in the presence of substantial changes in the ECG from one cardiac cycle to another. As in the case of adaptation of the comparison pattern wWav, those values for $\beta$ and $\gamma$ permit advantageous implementation in the form of a shift-and-subtract operation.

If adaptation of the threshold value is required the instantaneous value of detThr is replaced by one which is composed as follows: original threshold value multiplied by $(1-\beta)$ and that maximum value of the correlation coefficient, which is associated with the last-located feature, multiplied by $\beta$ and $\gamma$. Such adaptation of the threshold value results in exponential weighting of preceding values and asymptotic adaptation to a predetermined fraction $\gamma$ of the maximum of the correlation coefficient which is associated with the last-located feature of the ECG or IDZ.

In general terms it is preferred for that adaptation of the threshold value to be effected after each location of a signal feature. That reduces the probability of not identifying a feature for the reason that the amplitude of the feature changes and causes only little additional calculation complication and expenditure. As in the case of adaptation of the comparison pattern wWav however it is also possible to use for adaptation of the threshold value various strategies which make the time of adaptation of the threshold value dependent for example on the deviation of the respective maximum of the correlation coefficient from that which is associated with a previously detected feature.

A further matter of great significance for the apparatus are the methods of reducing the calculating expenditure and complication involved. That applies in particular having regard to the background that all internal operations of an implanted apparatus should cost as little energy as possible. Accordingly, the apparatus includes means for minimising for example the calculating power for calculation of correlation functions. Frequently that calculation power is afforded by a microprocessor. The fundamental considerations and the details of implantation are described hereinafter.

An important factor influencing calculation power is the sampling rate.

Calculation of a correlation function over a predetermined time interval includes, for each sampled signal value of the measurement signal, multiplication and summing of adjacent sampling values and the signal values and the comparison signal. As described hereinbefore, the comparison signal is so selected that it covers a short time interval which is of interest. The sampling rate determines the number of sampling or measurement signal values during the time interval which is of interest, and likewise also the number of signal values of the comparison signal. The consequence of this is that the number of multiplication and adding stages for the selected time interval of the measurement signal rises with the square of the sampling rate. For that reason, it is necessary to determine that minimum sampling rate which still supplies a usable result, and not to significantly exceed that value. Determining that sampling rate can be effectively implemented by means of computer simulations using a plurality of measurement signals which are already present and which were already recorded on patients and stored in databases. If that is implemented for feature identification and location and also for the analysis procedures described herein, the results show that sampling rates at or below 250 Hz are appropriate. Certain uses can require higher sampling rates, for example if the interest is for high-frequency signal features.

The energy consumption of each calculation is typically a linear function of the degree of calculation accuracy. For that reason, it is necessary to determine the minimum calculation accuracy which supplies usable results, and not to markedly exceed that value. As described above, this operation of determining the minimum level of calculation accuracy can be efficiently implemented by means of computer simulations. These have shown that there is no need for a degree of resolution of greater than 8 bits. That corresponds to a dynamic range or band width of 256 values.

The apparatus set forth herein uses the correlation function in order to detect signal features which are of interest in an ECG-signal or IDZ-signal and to accurately locate same or in order to implement specific signal shape analysis procedures and comparison operations. The computer simulations referred to above has shown that in practice both the numerical resolution and also the accuracy of correlation calculation can be substantially limited without adversely affecting the meaningfulness of the results. That forms the basis for various means for limiting the calculation load, which are described hereinafter.

Evaluation of a correlation function requires the formation of a product of successive pairs of signal values, which are formed by a signal value of the measurement signal and a signal value of the comparison signal. Embodiments of the apparatus which use for example an 8-bit representation of the signal values and a two's complement numbering would usually require the formation of a 16-bit product. In actual fact however, in such a system, an 8-bit product is sufficient for feature detection and location. That corresponds to truncation of those bits of the product, which represent orders of magnitude in the range of between 0 and 128. With that background in mind, it is also permissible to envisage alternative multiplication methods with limited resolution, which can reduce the calculation load, irrespective of whether those multiplication routines are implemented in hardware terms or in the form of a microcode of a processor.

An effective method of that kind uses a short table which is stored in a memory, the logarithm memory 28, of the apparatus, and contains integer values which correspond to logarithms of numbers. In an 8-bit two's complement system the table has for example 129 cells which are associated with the numbers m of 0 and 128. Each entry in the table contains that integer value which comes closest to $\ln(m) *128/\ln(128)$. Only the entry for m=0 is set to zero. When scaled in that way, the entries in the logarithm table cover the range between 0 and 128.

That table is used in the following manner to form a scaled product of x and y with a limited degree of resolution. As usual |..| represent absolute values:

1. read the content of the cell of the table associated with m=|x|
2. read the content of the cell of the table associated with m=|y|
3. add the two table entries
4. subtract 128
5. look for that cell in the table whose entry comes closest to the calculated value
6. take that value m with which the cell found in that way is associated as the result of the multiplication operation
7. provide the result with a sign corresponding to the sign of x and y.

The fourth step leads to a scaling factor of 1/128 which permits the use of a customary table both for the logarithm and also for the inverse function of the logarithm. In that way it is possible to find the product of x and y with a limited level of resolution by means of two memory reading steps, an addition operation, a subtraction operation and a six-stage binary search.

The signal processing methods used for the apparatus described herein, for forming the correlation function, presuppose the presence of locally outstanding values of the correlation function, which arise out of the similarity of the ECG-signal or IDZ-signal to be processed, with the comparison signal. In general, those local maxima of the signal corresponding to the correlation function occur when large signal values of the ECG-signal or IDZ-signal coincide with large values of the comparison function. As discussed above the usability of such a procedure has proven to be relatively independent of the absolute accuracy of calculation of the correlation coefficients. Therefore, a further effective method of reducing the computing load provides that, prior to calculation of the correlation coefficients, such products which contain signal values of the ECG-signal or IDZ-signal as factors which lie within a narrow band in the proximity of the center value of the signal are removed. The above-mentioned computer simulations have shown that, by means of such a procedure, with an 8-bit data system, with a sampling rate of 250 Hz, it is possible to achieve a 50% saving of the calculating load if, with an 8-bit signal, out of the 256 possible signal values, those which fall into a band of the width of 20 signal values are excluded from product calculation. Under those conditions the resulting adapted comparison signals involve a reliable coincidence with corresponding comparison signals which were calculated without leaving out the mean measurement signal values.

In a similar manner, to reduce the calculating load, it is possible to remove such products from calculation of the correlation coefficients, which contain the signal values of the comparison signal as factors which fall into a narrow band near the center value of the comparison signal. In order in that situation to observe the condition that the sum of all signal values of the comparison signal is zero, signal values near the center value can already be set to zero in the adaptation operation or when forming the comparison signal, after the standardisation operation.

For feature detection the threshold value comparison means 32 output an identification signal only when the correlation signal comprising the correlation coefficients is initially above the threshold value and then exhibits a zero-passage. At that time, the precise location of those events is not of critical significance as the occurrence thereof triggers accurate feature location by means of the location detector 32. Therefore, and having regard to the usual structure of ECG- and IDZ-signals, it is acceptable if, to form the identification signal, only each second correlation signal value is processed, whereby a 50% reduction in the calculating load is achieved.

When using the apparatus described herein, it will usually happen that signal features which are of interest are of a relatively long duration and change only slowly. An example in this respect is the T-waves in an ECG-signal, which represent re-polarisation. In a system with a sampling rate of 250 Hz and an assumed length of the comparison signal of 16 signal values, the duration of the comparison signal corresponds to 64 ms of the ECG-measurement signal. That is not suitable for reliable location of features which extend over 100 ms or more, like the above-mentioned T-waves. A possible resolution for that problem would be to prolong the comparison signal. This means that the comparison signal includes more signal values so that the computing load increases. An effective alternative provides for using only each n-th signal value of the measurement signal for the calculation, if it is known that the signal feature being sought has little usable information in a frequency range which corresponds to the sampling rate divided by 2 n. In that way the processing complication and expenditure for the situation in which features of long duration which change slowly are of interest can be effectively reduced.

The mode of operation of the apparatus for feature detection and location in ECG- or IDZ-signals will be described hereinafter.

The mode of operation involved is based on forming correlation coefficients between short portions of the measurement signal which occur in mutually overlapping succession, and a comparison signal, the length of which corresponds to the portions of the measurement signal. Portion-wise comparison of the measurement signal with the comparison signal gives a sequence of correlation coefficients, each of which is precisely associated with a portion of the measurement signal and which together give a correlation signal comprising discrete correlation values.

The criterion for feature detection requires that at least one correlation coefficient exceeds a predetermined positive threshold value and that thereupon a zero-passage of the correlation signal subsequently follows. If those two conditions are met, a feature is deemed to be roughly identified. Then, among all those correlation coefficients which satisfy the above-mentioned conditions, the largest one is sought. That local maximum of the correlation signal then identifies the location of the signal feature to be detected. Once the location has been found it is stored for further analysis in a memory of the apparatus. By way of the above-mentioned association of each correlation coefficient of the correlation signal with precisely one portion of the measurement signal, the procedure by means of the location provides for identifying precisely one portion of the measurement signal which has the greatest degree of similarity to the comparison signal in the region in which the detection conditions are met. In that way it is possible to precisely determine the location of a signal feature in the measurement signal in a sampling step. With a sampling rate of 250 Hz, this means that the location of a signal feature is accurate to 4 ms.

The shape of the comparison signal and also the detection threshold value are continuously adapted in order to take account of changes in the measurement signal shape. The nature of the adaptation operation has been described hereinbefore. Adaptation of the comparison signal to a measurement signal makes it possible to identify and locate a signal feature with a high degree of probability and as precisely as possible, more specifically even when the measurement signal is subjected to fluctuations or for example has noise superimposed thereon.

For the following description of the operating procedure in the apparatus, in particular the access to the first memory 22 which contains the individual measurement values which represent the measurement signal or at least portions thereof is of significance. Access to the first memory 22 is effecteed by means of an index indicator, bIndex. That index indicator firstly points to a memory location which is as many memory locations away from the first memory location 22, as corresponds to the number of signal values which form the comparison signal. The number of those signal values is denoted by wLen. If a new measurement value for the measurement signal is written into the first memory before processing of a preceding signal value is terminated, the indicator bindex points to the preceding measurement signal value.

Signal processing in the apparatus takes place in the following way:
1. Firstly a predetermined comparison pattern iWav is written into the memory for the comparison pattern wWav. That is initialisation of the comparison pattern.
2. Initialisation of the threshold value detThr for the feature detection operation is effected by a procedure whereby that threshold value is set to an initial threshold value iDetThr and that value is written into the threshold value memory 36. Preferably, the initial threshold value iDetThr is a relatively low threshold value which ensures that a signal feature is actually identified. A typical value for a system which operates with an 8-bit measurement signal and in which the number of signal values of the comparison signal wLen is 16, is 20 for the threshold value.
3. Then the identification signal detState is set to '0'. The identification signal can assume overall three states of which the state '0' is the first and characterises the state in which feature detection is not active.

4. The value of the greatest correlation coefficient in a portion of the correlation signal which satisfies the above-described detection conditions is maxccVal. That value is set in initialisation to the largest permitted negative value.

5. The moment in time at which the value maxccVal occurs in relation to the measurement signal, as '0', the location in respect of time of the local maximum of the correlation signal, is identified as maxccLoc and is set to '0' in the initialisation procedure.

6. The comparison signal wWav is used for each measurement signal value of the measurement signal which occurs at the memory location of the first memory 22, which is identified by bindex, in order to form the correlation coefficient ccVal by way of the number wLen of the measurement signal values forming the comparison signal, which precede the measurement signal value identified by bindex, that is to say which were recorded before that measurement signal value.

7. If ccVal is greater than maxccVal, the value of maxccVal is set to the value of ccVal and the location of the corresponding signal value of the measurement signal is stored as maxccLoc.

8. If the value of ccVal is greater than that of detThr and if at the same time detState is '0', detState is set to '1'. The identification signal is thus of the value '1'. That means that signal identification is now active.

9. If the value ccVal is less than zero and the state of the identification signal detState is '1', that state detState is set to '2'. The state '2' of the identification signal indicates that the measurement signal now satisfies the detection conditions, that is to say that a signal feature which is of interest is detected. In the next step, the location of that feature is determined as precisely as possible. That is effected by a procedure whereby the largest value for ccVal is sought for the following measurement signal values corresponding to the number wLen of the signal values of the comparison signal, which follow the measurement signal value identified as maxccLoc.

10. If the state of the identification signal detState is '2', the following steps are executed, otherwise the procedure reverts to step 6:

10.1 Use the comparison signal wWav in order to calculate the correlation coefficient ccVal by way of the number of measurement signal values which follow the measurement signal value identified by maxccLoc, said number corresponding to the number wLen of the signal values of the comparison signal.

10.2 If in one of the steps in accordance with 10.1 it is found that ccval exceeds the value of maxccVal, the value of maxccVal is set to the value of ccVal and the location of the corresponding measurement signal value is stored as featureLoc. The definitive value of featureLoc then represents the most precise value for the occurrence in respect of time of a feature to be detected, and therefore forms a time stamp for that signal as soon as the comparison signal wWav has adapted to the measurement signal structure.

10.3 The located signal feature and its time stamp are then stored for the further analysis procedure.

10.4 If a comparison signal adaptation operation is provided, then after location of a signal feature adaptation of the comparison signal is executed as follows:

10.4.1 Form a new comparison signal wWav with the predetermined comparison signal adaptation parameter $\alpha<1$ in the memory of the comparison signal adaptation unit 40 having regard to wWav and the located measurement signal portion of the length (number of the measurement signal values) wLen as follows: multiply the signal values of wWav by $(1-\alpha)$ and add thereto the number, corresponding to wLen, of the measurement signal values at the location featureLoc, multiplied by $\alpha$.

10.4.2 Scale the result in such a way that the new comparison signal wWav has the maximum dynamic range which is predetermined by the measuring device for the measurement signal so that the sum of the signal values of the comparison signal is zero. Write the new comparison signal wWav formed in that way into the second memory 26.

10.4.3 Form a new threshold value on the basis of the threshold value adaptation parameter $\beta$ and the threshold value asymptote $\gamma$ in the memory of the threshold value adaptation unit 34 as follows: multiply the original threshold value detThr by $(1-\beta)$ and add thereto $\beta * \gamma *$ maxccVal. Store the new threshold value obtained in that way in the threshold value memory 36.

10.4.4 If necessary store the freshly formed comparison signal wWav in a memory for further analysis. The adapted comparison signal contains the exponential weighted statistical information about the last-located signal features which can be of interest for some uses.

10.5 Set the memory index bindex to a position which is by tRef/tSamp memory locations in front of featureLoc, wherein tRef is the desired refractory time of the measurement channel while tSamp is the sampling rate. In this case, according to choice, as indicated in the opening part of this specification, it is possible to leave out certain measurement signal values for the calculation of the correlation coefficient or it is possible to delay the processing in order to implement a refractory time. The freshly formed memory index bindex however should be in front of the first memory location of the memory 22 at least by a number of memory locations, which corresponds to wLen, in order to be able to satisfactorily implement the next feature location operation.

10.6 Revert to step 3. In the case of a detection loss a predetermined strategy can be applied for recovery of the data before reverting to step 3.

A strategy for data recovery in the event of data loss will now be described hereinafter.

A loss of feature identification can occur for various reasons, also outside a clinic, for example in medical emergency situations. If that detection loss persists for a given time, that is to say if no signal feature is identified for a period of time, so that adaptation of the comparison signal and the detection threshold also no longer takes place, an autonomous strategy must be provided in order to restore the desired mode of operation. There are various possible options for that purpose, which have certain points in common:

1. set detThr=iDetThr or to another predetermined low value;
2. trigger a comparison signal adaptation operation from one cardiac cycle to another; or
3. initialise the comparison signal wWav afresh.

The purpose of 1. is to maximise the probability of feature detection in the channel in question. The aim of 2. is to ensure rapid adaptation of the comparison signal to detected signal features. The aim of 3. is to predetermine a comparison signal which is suitable for the detection of a large number of possible features. That comparison signal can correspond to the original comparison signal iWav, as was described hereinbefore, or it can be a special comparison signal for the event of a detection loss.

The way in which the apparatus implements the signal analysis operation already referred to above will now be described hereinafter.

One aspect of signal analysis is analysis of the time relationships between the left and right atria or the left and right ventricles of a heart. The apparatus can be used for that purpose in various ways, depending on the nature of data recording in the various chambers. The following two examples should illustrate this.

Figure 5:
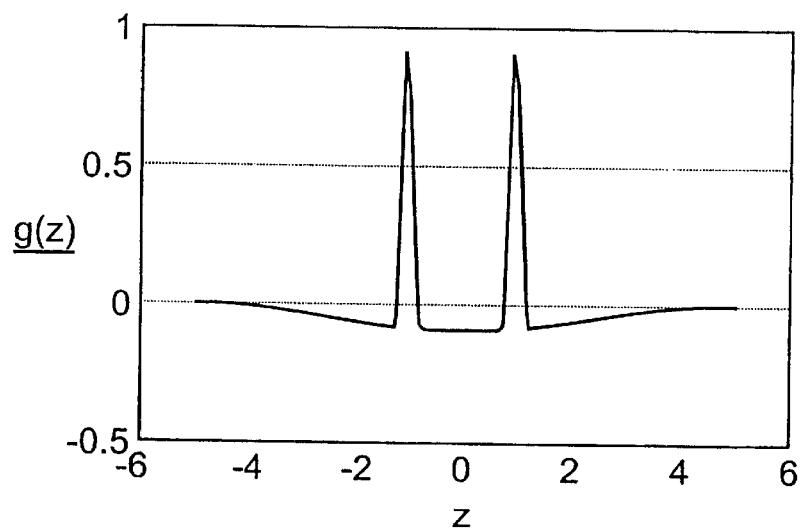
FIG. 5 shows a comparison signal of bimodal structure.
Figure 6A:
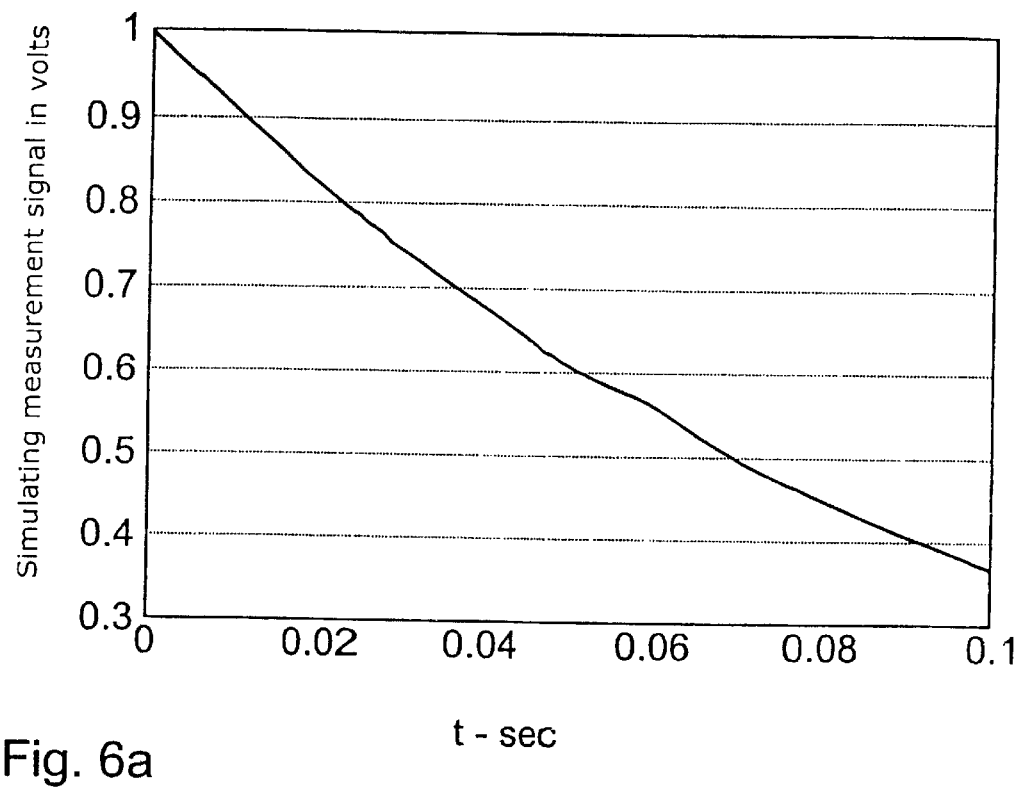
FIGS. 6a–d show the result of simulation of a detector for an evoked cardiac reaction.
Figure 6B:
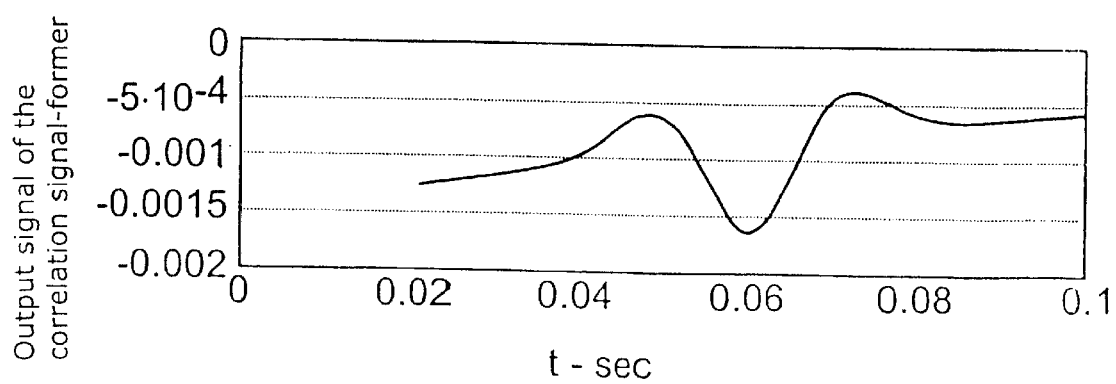
Figure 6C:
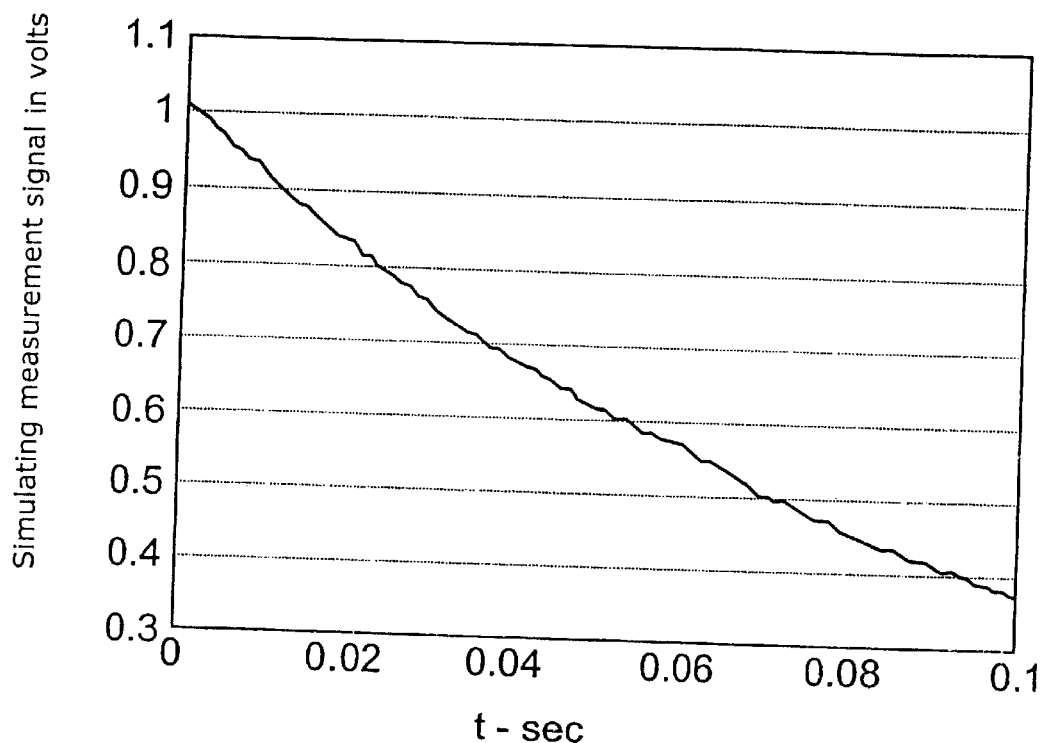
Figure 6D:
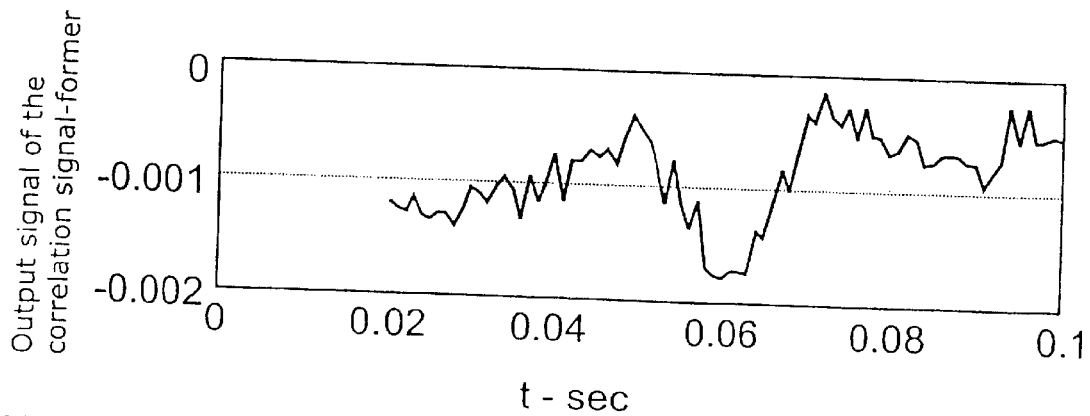

If two separate channels are available for the two heart chambers, the conduction time for example from the right to the left atrium can be implemented by processing a signal value sequence which is composed of values of both signal pick-ups and which begins with the signal values of the right atrium and continues with those of the left atrium. The predetermined comparison signal is bimodal and has two maximum values as the example in FIG. 5 shows. The spacing in respect of time of those two maximum values corresponds to the expected value for the conduction time. For calculation of the correlation coefficients, firstly the first half of the signal values of the comparison signal are used, which contain the first maximum and calculated with those measurement signal values which originate from the right atrium. The second half of the signal values of the comparison pattern which contain the second maximum thereof are then calculated with signal values which originate from the left atrium. The result is detection of an artificial feature which is a bimodal composite from the two channels and contains events which are associated with both chambers. The above-described adaptation of the comparison pattern has the result that it increasingly reflects the dual structure of the composite. Each composite can then be analysed in terms of the spacing in respect of time of the right-atrial and left-atrial events. That applies in regard to the composite of the measurement signal. If a statistical mean value is sought, for example for the conduction time, then instead of a composite from the right-atrial and left-atrial measurement signals, it is also possible to analyse the adapted comparison signal. In both cases, analysis includes the identification of two local maxima and determination of the spacing in respect of time thereof. That time spacing of the local maxima corresponds to the conduction time.

If only one channel is available for two chambers, it is not possible to apply the above-described strategy. Instead, each detected feature of the common channel has to be analysed in order to determine the time spacing of individual right-atrial and left-atrial events. As described hereinbefore that can be implemented alternatively by analysis of the measurement signal or by analysis of the comparison signal. With these analysis procedures it is also important to detect two local maxima as well as the spacing in respect of time thereof. The analysis procedures involved can however be more complex because of the superimposition effects of the signals in a common measurement channel.

Besides the operation of determining the conduction time, a further analysis operation lies in classification of detected features. That can be effected by means of various comparison signals which are each characteristic in respect of a given signal class. The comparison signal database 42 can also serve for that purpose.

| Appendix | |
|---|---|
| α | degree of adaptation for comparison signal adaptation |
| β | degree of adaptation for detection threshold adaptation |
| γ | adaptation asymptote for detection threshold value |
| bIndex | index indicator for the first memory 22 |
| ccVal | value of a correlation coefficient |
| maxccVal | maximum local correlation coefficient in the portion of the correlation signal, for which the conditions of feature detection are satisfied |
| maxccLoc | location in respect of time of maxccVal |
| featureLoc | location in respect of time of a located feature |
| detState | logic state of the detection signal |
| detThr | Value of the detection threshold value |
| iDetThr | original predetermined value of the detection threshold |
| tRef | desired refractory time of the measurement channel |
| tSamp | sampling rate for the measurement signal |
| wLen | number of signal values of the comparison signal |
| wWav | adapted comparison signal |
| iWav | original predetermined comparison signal prior to adaptation |

What is claimed is:

1. An apparatus for processing body signals, comprising;
    at least one sensor for picking up electrical signals from a living body,
    means for preparing for further processing picked-up signals;
    at least one first memory for a picked-up measurement signal or portion thereof,
    at least one second memory that contains a predeterminable comparison signal that is finite in respect of time, and
    a means for signal comparing that is connected to the second memory and the first memory and that is adapted for sliding comparison of signal portions, which overlap in respect of time, of the measurement signal in the first memory to the comparison signal stored in the second memory and for output of a correlation coefficient representing the similarity of each compared signal portion of the measurement signal to the comparison signal.

2. The apparatus as set forth in claim 1 characterised in that an integral in relation to time or its sum of the time-discrete signal values is zero.

3. The apparatus as set forth in claim 1 characterised in that the signal comparing means is connected to a logarithm memory that contains tables of logarithms for the values of the measurement and comparison signals, wherein the signal comparing means are so designed for forming the correlation coefficients that they execute multiplication of a value of the comparison signal from the second memory by a corresponding value of the measurement signal from the first memory in such a way that firstly the logarithms of the values to be multiplied themselves or the values respectively closest thereto are read out of the logarithm memory and then the two logarithms are added.

4. The apparatus of claim 3 further comprising a detection means that is connected to the signal comparison means and that is designed to detect maximum values and/or zero-passages of a signal formed by the correlation coefficients.

5. The apparatus of claim 4 further comprising a means for comparing threshold values that is connected to the signal comparing means and a threshold value memory containing a threshold value and is designed to output an identification signal as soon as the correlation coefficient outputted by the signal comparing means exceeds the threshold value.

6. The apparatus of claim 5 wherein the threshold value comparing means is additionally so designed that it outputs an identification signal when a correlation coefficient for a first signal portion from the first memory exceeds the threshold value and for a second signal portion which is recorded in respect of time after the first signal portion reaches or is below the value zero.

7. The apparatus of claim 6 further comprising a locating means which is connected to the threshold value comparing means and the detection means and which is so designed that it associates a location signal with that signal portion of the measurement signal in the first memory, in respect of which the signal formed by correlation coefficients has a maximum within that portion of the signal formed by the correlation coefficients, for which the threshold value comparing means output an identification signal.

8. The apparatus as set forth in claim 7 further comprising threshold value-forming means which is connected to the threshold value memory and the locating means and is so designed that it forms a new threshold value after the occurrence of a location signal in such a way that the correlation coefficient associated with the location signal is involved in weighted fashion in the formation of the new threshold value.

9. The apparatus of claim 8 further comprising a means for forming a new comparison signal, which is connected to the second memory and is so designed that a measured signal portion which corresponds to a signal feature to be detected is transformed to the comparison signal in such a way that its integral in relation to time is zero and the comparison signal formed in that way is transferred into the second memory.

10. The apparatus of claim 9 further comprising comparison signal-adaptation means for adaptation of the comparison signal which is connected to the first memory, the second memory and the locating means and is so designed that it forms a new adapted comparison signal when the locating means output a location signal, wherein the adapted comparison signal is formed using that measurement signal portion from the first memory, with which the location signal is associated.

11. The apparatus of claim 10 wherein the comparison signal-adaptation means is so designed that the comparison signal valid prior to adaptation, for forming the comparison signal valid after adaptation, is weighted with a factor $1-\alpha$ while that signal portion in the first memory which has triggered the identification signal by means of the signal comparison means and the locating means, is involved with a weighting factor $\alpha$ in the comparison signal which is valid after adaptation.

12. The apparatus of claim 11 wherein the comparison signal-forming means and/or the comparison signal-adaptation means are so designed that the comparison signal which is so formed or adapted is standardised in such a way that the amplitude thereof corresponds to the maximum amplitude of the measurement signal.

13. The apparatus of claim 12 further comprising a database which contains a plurality of comparison signals and is connected to the second memory in such a way that comparison signals can be transferred from the database into the second memory and vice-versa.

14. The apparatus of claim 13 further comprising means for analysis of the characterising properties of the preferably adapted comparison signal.

15. The apparatus of claim 14 wherein a first said at least one sensor is for cardiac signals associated with the left ventricle or atrium and a second said at least one sensor is for cardiac signals associated with the right ventricle or atrium, means connected to said first and second said at least one sensors for forming a bimodal signal from the two cardiac signals in such a way that the bimodal signal contains a feature of the first signal prior to conduction into the respective other ventricle or atrium and the corresponding feature after conduction thereof, so that the feature is contained in the bimodal signal at a spacing in respect of time corresponding to the conduction time on the one hand in its form prior to conduction and on the other hand in its form after conduction, and characterised in that the second memory contains a bimodal comparison signal which can be adapted to the bimodal signal so that after adaptation of the bimodal comparison signal to the bimodal signal the conduction time can be determined by analysis of the comparison signal.

\* \* \* \* \*

UNITED STATES PATENT AND TRADEMARK OFFICE
CERTIFICATE OF CORRECTION

PATENT NO.    : 6,577,892 B2
DATED         : June 10, 2003
INVENTOR(S)   : Richard A. Schomburg It is certified that error appears in the above-identified patent and that said Letters Patent is hereby corrected as shown below:

<u>Title page,</u>
Item [73], Assignee, replace "Biotonik" with -- Biotronik --.

Signed and Sealed this

Nineteenth Day of August, 2003

JAMES E. ROGAN
*Director of the United States Patent and Trademark Office*